US00PP20420P2

(12) United States Plant Patent
Michalik

(10) Patent No.: US PP20,420 P2
(45) Date of Patent: Oct. 13, 2009

(54) ***GERANIUM* PLANT NAMED 'PACRIC'**

(50) Latin Name: *Pelargonium peltatum*
Varietal Denomination: Pacric

(75) Inventor: Andrea Michalik, Dresden (DE)

(73) Assignee: Elsner PAC Jungpflanzen, Dresden (DE)

( * ) Notice: Subject to any disclaimer, the term of this patent is extended or adjusted under 35 U.S.C. 154(b) by 0 days.

(21) Appl. No.: 12/214,643

(22) Filed: Jun. 20, 2008

(51) Int. Cl.
*A01H 5/00* (2006.01)

(52) U.S. Cl. ..... Plt./332

(58) Field of Classification Search ..... Plt./324, Plt./332
See application file for complete search history.

*Primary Examiner*—Susan B McCormick Ewoldt
(74) *Attorney, Agent, or Firm*—C. A. Whealy

(57) ABSTRACT

A new and distinct cultivar of Ivy *Geranium* plant named 'Pacric', characterized by its upright, outwardly spreading to trailing and rounded plant habit; freely branching habit; vigorous growth habit; dark green-colored leaves; freely flowering habit; red purple-colored flowers; and relatively good garden performance.

1 Drawing Sheet

Botanical designation: *Pelargonium peltatum.*
Cultivar denomination: 'Pacric'.

BACKGROUND OF THE INVENTION

The present invention relates to a new and distinct cultivar of Ivy *Geranium,* botanically known as *Pelargonium peltatum,* and hereinafter referred to by the name 'Pacric'.

The new Ivy *Geranium* is a product of a planned breeding program conducted by the Inventor in Dresden, Germany. The objective of the breeding program is to create new early flowering flowering Ivy *Geranium* cultivars with good vigor and attractive flower coloration.

The new Ivy *Geranium* originated from a cross-pollination made by the Inventor in Dresden, Germany during the summer of 2002 of two unnamed proprietary selections of *Pelargonium peltatum,* not patented. The cultivar Pacric was discovered and selected by the Inventor as a flowering plant from within the progeny of the stated cross-pollination in a controlled greenhouse environment in Dresden, Germany during the spring of 2003.

Asexual reproduction of the new Ivy *Geranium* by vegetative terminal cuttings in a controlled greenhouse environment in Dresden, Germany since December, 2003, has shown that the unique features of this new Ivy *Geranium* are stable and reproduced true to type in successive generations.

SUMMARY OF THE INVENTION

Plants of the new Ivy *Geranium* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Pacric'. These characteristics in combination distinguish 'Pacric' as a new and distinct cultivar of Ivy *Geranium:*

1. Upright, outwardly spreading to trailing and rounded plant habit.
2. Freely branching habit.
3. Vigorous growth habit.

4. Dark green-colored leaves.
5. Freely flowering habit.
6. Red purple-colored flowers.
7. Relatively good garden performance.

Plants of the new Ivy *Geranium* differ primarily from plants of the parent selections in plant vigor and flower color.

Plants of the new Ivy *Geranium* can be compared to plants of the *Pelargonium peltatum* 'Pennea', disclosed in a U.S. Plant patent application Ser. No. 09/733,016, now abandoned. In side-by-side comparisons conducted in Dresden, Germany, plants of the new Ivy *Geranium* differed from plants of 'Pennea' in the following characteristics:

1. Plants of the new Ivy *Geranium* were not as vigorous as plants of 'Pennea'.
2. Plants of the new Ivy *Geranium* were more freely branching than plants of 'Pennea'.
3. Flowers of plants of the new Ivy *Geranium* had fewer petals than flowers of plants of 'Pennea'.
4. Plants of the new Ivy *Geranium* and 'Pennea' differed slightly in flower color.

BRIEF DESCRIPTION OF THE PHOTOGRAPH

The accompanying colored photograph illustrates the overall appearance of the new Ivy *Geranium*, showing the colors as true as it is reasonably possible to obtain in colored reproductions of this type. Colors in the photograph may differ slightly from the color values cited in the detailed botanical description which accurately describe the colors of the new Ivy *Geranium*. The photograph comprises a side perspective view of a typical flowering plant of 'Pacric' grown in a container.

DETAILED BOTANICAL DESCRIPTION

The aforementioned photograph and following observations, measurements and values describe plants grown in Dresden, Germany in a glass-covered greenhouse during the winter and spring and under conditions which closely approximate commercial Ivy Geranium production. During the production of the plants, day temperatures ranged from 18° C. to 20° C., night temperatures averaged 18° C. and light levels ranged from 15 kilolux to 100 kilolux. Plants were five months from planting when the photograph and description were taken. In the detailed description, color references are made to The Royal Horticultural Society Colour Chart, 1995 Edition, except where general terms of ordinary dictionary significance are used.

Botanical classification: *Pelargonium peltatum* 'Pacric'.

Parentage:

*Female, or seed, parent.*—Unnamed proprietary selection of *Pelargonium peltatum*, not patented.

*Male or pollen parent.*—Unnamed proprietary selection of *Pelargonium peltatum*, not patented.

Propagation:

*Type.*—By vegetative terminal cuttings.

*Time to initiate roots, summer.*—About 18 days at temperatures of 20° C.

*Time to initiate roots, winter.*—About 22 days at temperatures of 20° C.

*Time to produce a rooted young plant, summer and winter.*—About 30 days at temperatures of 20° C.

*Root description.*—Fine, fibrous; white in color.

*Rooting habit.*—Freely branching; dense.

Plant description:

*Plant/growth habit.*—Upright, outwardly spreading to trailing and rounded plant habit; densely foliated. Vigorous growth habit. Freely basal branching habit with about seven lateral branches developing per plant:

*Plant height, to top of umbels.*—About 25 cm.

*Plant height, to top of leaves.*—About 15 cm.

*Plant width.*—About 30 cm.

*Lateral branches.*—Length: About 15 cm. Diameter: About 4 mm. Internode length: About 3 cm to 4 cm. Texture: Slightly pubescent. Color: Close to 144A.

Foliage description:

*Arrangement.*—Alternate or opposite; simple.

*Length.*—About 4 cm.

*Width.*—About 7 cm.

*Shape.*—Ivy-shaped, lobed.

*Apex.*—Acute.

*Base.*—Cordate; partially imbricate.

*Margin.*—Entire with lobes.

*Venation pattern.*—Palmate.

*Texture, upper surface.*—Smooth, glabrous.

*Texture, lower surface.*—Slightly pubescent.

*Color.*—Developing and fully expanded foliage, upper surface: Close to 137A; venation, close to 144A. Developing and fully expanded foliage, lower surface: Close to 137C; venation, close to 144A. Zonation pattern: Weak. Location from margin: About 3 cm. Width: About 1 cm. Color: Close to 200D. Petiole: Length: About 5 cm. Diameter: About 2 mm to 3 mm. Texture, upper and lower surfaces: Pubescent. Color, upper and lower surfaces: Close to 144A.

Flower description:

*Flower arrangement.*—Rotate flowers arranged in rounded hemispherical umbels arising from apical leaf axils. Umbels displayed above the foliage on strong peduncles. Flowers face upright to outward; flowers flat. Flowers not fragrant.

*Quantity of flowers.*—Freely flowering habit; numerous umbels develop per plant each with about 16 flower buds and open flowers.

*Flowering season.*—Year-round under greenhouse conditions. In the garden in Dresden, Germany, flowering is continuous from May until frost in the autumn. Flowers persistent.

*Flower longevity.*—Individual flowers last about six to ten days on the plant; umbels last about three to four weeks on the plant.

*Umbel height.*—About 5 cm.

*Umbel diameter.*—About 9 cm.

*Flower diameter.*—About 5 cm.

*Flower depth (height).*—About 2 cm.

*Flower buds.*—Length: About 1 cm. Diameter: About 5 mm. Shape: Roughly elliptic. Color: Close to 144A.

*Petals.*—Quantity per flower: About ten. Length: About 3 cm. Width: About 2 cm. Shape: Obovate. Apex: Rounded. Base: Attenuate. Margin: Entire. Texture, upper and lower surfaces: Smooth, glabrous; velvety. Color: When opening and fully opened, upper surface: Close to 66A; towards the base, close to 55C; venation, close to 66A. When opening and fully opened, lower surface: Close to 55A; towards the base, close to 55C; venation, close to 55A.

*Petaloids.*—Quantity per flower: None to about four. Length: About 1 cm to 1.5 cm. Width: About 5 mm to 15 mm. Shape: Irregular. Apex: Obtuse. Base: Attenuate. Margin: Entire. Texture, upper and lower surfaces: Smooth, glabrous; velvety. Color: When opening and fully opened, upper surface: Close to 66A; towards the base, close to 66A; venation, close to 66A. When opening and fully opened, lower surface: Close to 55A; towards the base, close to 55A; venation, close to 55A.

*Sepals.*—Quantity per flower: Five, arranged in a single whorl. Length: About 1.5 cm. Width: About 4 mm. Shape: Lanceolate. Apex: Acute. Margin: Entire. Texture, upper and lower surfaces: Slightly pubescent. Color, upper and lower surfaces: Close to 144A.

*Peduncle (umbel stem).*—Length: About 12 cm. Diameter: About 3 mm. Strength: Strong. Angle: Mostly erect to outwardly spreading. Texture: Slightly pubescent. Color: Close to 144A.

*Pedicel (individual flower stem).*—Length: About 2 cm. Diameter: About 2 mm. Strength: Moderately strong; flexible. Texture: Slightly pubescent. Color: Close to 200B.

*Reproductive organs.*—Androecium: Stamen quantity per flower: About seven. Anther length: About 2 mm. Anther shape: Tubular, elongated. Anther color: Close to 200A. Pollen amount: Moderate. Pollen color: Close to 163C. Gynoecium: Pistil quantity per flower: One. Pistil length: About 1 cm. Stigma shape: Six to eight-parted. Stigma color: Close to 60A. Style length: About 3 mm. Style color: Close to 60C. Ovary color: Close to 148B.

*Seeds.*—Seed development has not been observed on plants of the new Ivy *Geranium*.

Disease/pest resistance: Plants of the new Ivy *Geranium* have not been observed to be resistant to pathogens and pests common to Ivy *Geraniums*.

Garden performance: Plants of the new Ivy *Geranium* have been observed to tolerate rain, wind and temperatures ranging from about 1° C. about 35° C. to 40° C. and have demonstrated relatively good garden performance.

It is claimed:

1. A new and distinct Ivy *Geranium* plant named 'Pacric' as illustrated and described.

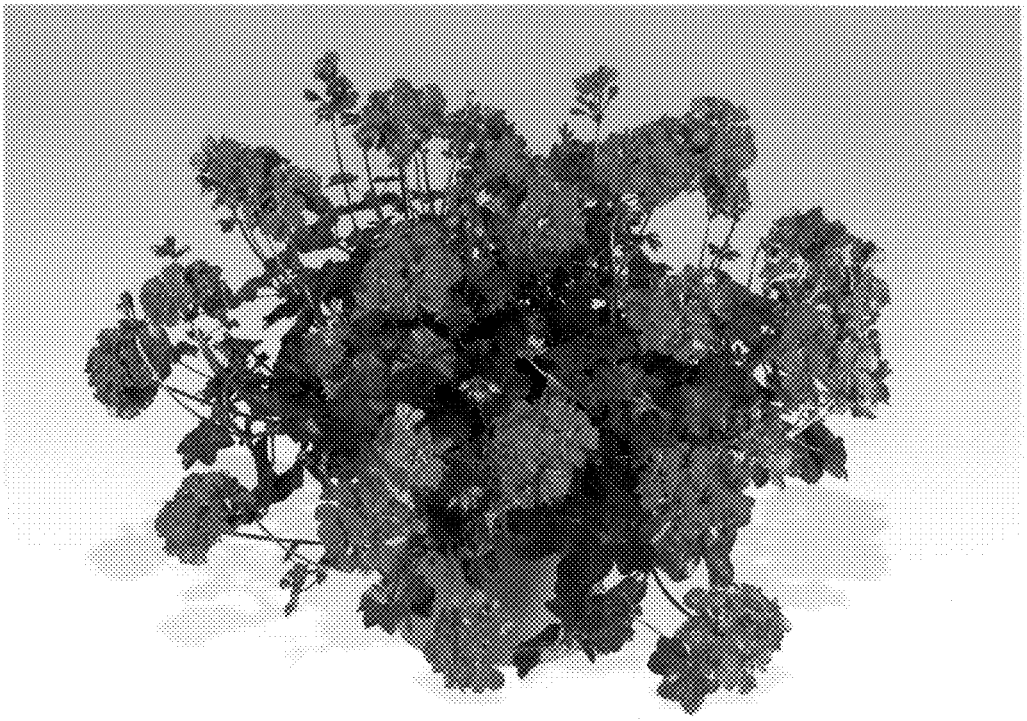

* * * * *